United States Patent
Rondano et al.

(10) Patent No.: US 9,921,179 B2
(45) Date of Patent: Mar. 20, 2018

(54) FLUIDS DETECTION SENSOR AND RAIL, IN PARTICULAR FOR AUTOMOTIVE FUELS

(75) Inventors: Matteo Rondano, Alessandria (IT); Luiz Wagner Main, Sao Paulo (BR); Mauro Zorzetto, Casale Monferrato (IT)

(73) Assignee: ELTEK S.P.A., Casale Monferrato (AL) (IT)

( * ) Notice: Subject to any disclaimer, the term of this patent is extended or adjusted under 35 U.S.C. 154(b) by 470 days.

(21) Appl. No.: 14/006,609

(22) PCT Filed: Mar. 23, 2012
(Under 37 CFR 1.47)

(86) PCT No.: PCT/IB2012/051408
§ 371 (c)(1),
(2), (4) Date: Apr. 24, 2015

(87) PCT Pub. No.: WO2012/127454
PCT Pub. Date: Sep. 27, 2012

(65) Prior Publication Data
US 2015/0226700 A1 Aug. 13, 2015

(30) Foreign Application Priority Data
Mar. 24, 2011 (IT) .............. TO2011A0258

(51) Int. Cl.
*G01N 27/416* (2006.01)
*F02M 55/02* (2006.01)
(Continued)

(52) U.S. Cl.
CPC ....... *G01N 27/4166* (2013.01); *F02M 55/025* (2013.01); *F02M 65/00* (2013.01);
(Continued)

(58) Field of Classification Search
CPC ............. F02M 57/005; F02M 2200/24; F02M 51/005; F02M 26/46; F02M 2200/247;
(Continued)

(56) References Cited

U.S. PATENT DOCUMENTS

| 4,555,661 A | 11/1985 | Benson et al. |
| 4,627,906 A | 12/1986 | Gough |

(Continued)

FOREIGN PATENT DOCUMENTS

EP 1 443 207 A2 8/2004

OTHER PUBLICATIONS

International Search Report dated Oct. 1, 2012, issued in PCT Application No. PCT/IB2012/051408, filed Mar. 23, 2012.
(Continued)

*Primary Examiner* — Long T Tran
(74) *Attorney, Agent, or Firm* — Workman Nydegger

(57) ABSTRACT

A sensor for detecting the properties of the fuel of an internal combustion engine includes at least one pair of internal electrodes (12, 13), extending in an axial direction relative to a further or third external electrode (14) which surrounds them. The invention also relates to a fuel rail (2) to which the sensor may be mounted, and a method for detecting the properties of the fluid.

26 Claims, 13 Drawing Sheets

(51) Int. Cl.
*G01N 33/28* (2006.01)
*F02M 65/00* (2006.01)
*G01N 27/30* (2006.01)

(52) U.S. Cl.
CPC ......... *G01N 27/30* (2013.01); *G01N 33/2835* (2013.01); *F02M 2200/24* (2013.01); *F02M 2200/8023* (2013.01); *F02M 2200/853* (2013.01)

(58) Field of Classification Search
CPC .. F02M 65/001; F02M 63/0225; F02M 65/00; G01N 27/221; G01N 33/2829; G01N 27/226; G01N 27/228; G01N 27/4073; G01N 27/4071; G01N 27/4074; G01N 15/0656; G01N 27/30; G01N 33/2835
USPC ................ 123/468, 445, 456, 478; 204/412; 205/787
See application file for complete search history.

(56) References Cited

U.S. PATENT DOCUMENTS

| | | | |
|---|---|---|---|
| 4,905,655 A | 3/1990 | Maekawa | |
| 4,939,468 A | 7/1990 | Takeuchi | |
| 5,140,965 A | 8/1992 | Nogi et al. | |
| 6,057,693 A | 5/2000 | Murphy et al. | |
| 6,803,775 B2* | 10/2004 | Sanchez | G01N 33/2852 324/515 |
| 6,885,199 B2* | 4/2005 | Desmier | G01N 33/2829 324/663 |
| 8,171,802 B2* | 5/2012 | Henderson | G01F 23/24 73/861.12 |
| 2003/0141882 A1 | 7/2003 | Zou et al. | |
| 2005/0253599 A1* | 11/2005 | Vanzullen | G01N 27/226 324/686 |
| 2008/0143347 A1* | 6/2008 | Casey | G01N 33/2852 324/663 |
| 2008/0295804 A1* | 12/2008 | Matas | F02M 55/025 123/456 |
| 2009/0095052 A1* | 4/2009 | Inoue | F02D 41/1454 73/23.32 |
| 2009/0153154 A1 | 6/2009 | Hernandez et al. | |
| 2010/0252002 A1* | 10/2010 | Fujino | F02M 47/027 123/472 |
| 2010/0252659 A1* | 10/2010 | Fujino | F02M 47/027 239/585.5 |
| 2010/0300406 A1 | 12/2010 | Harvey et al. | |
| 2011/0011184 A1* | 1/2011 | Henderson | G01F 1/007 73/861.12 |
| 2011/0146619 A1* | 6/2011 | McAlister | F02M 51/0675 123/297 |
| 2011/0290013 A1* | 12/2011 | Naydenov | G01F 23/266 73/304 C |

OTHER PUBLICATIONS

Italian Search Report dated Nov. 2, 2011, issued in Italian Application No. TO20110258, filed Mar. 24, 2011.

* cited by examiner

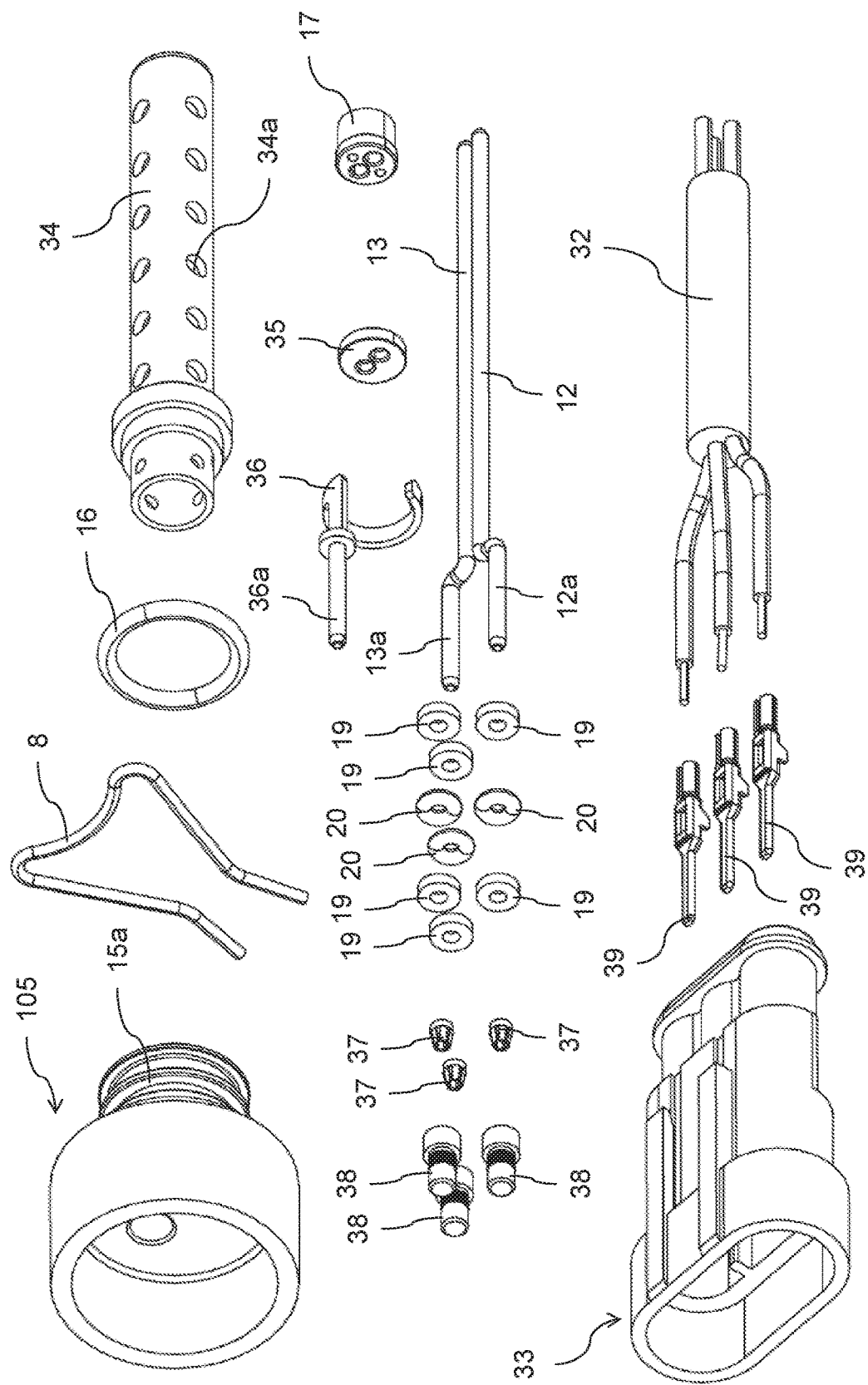

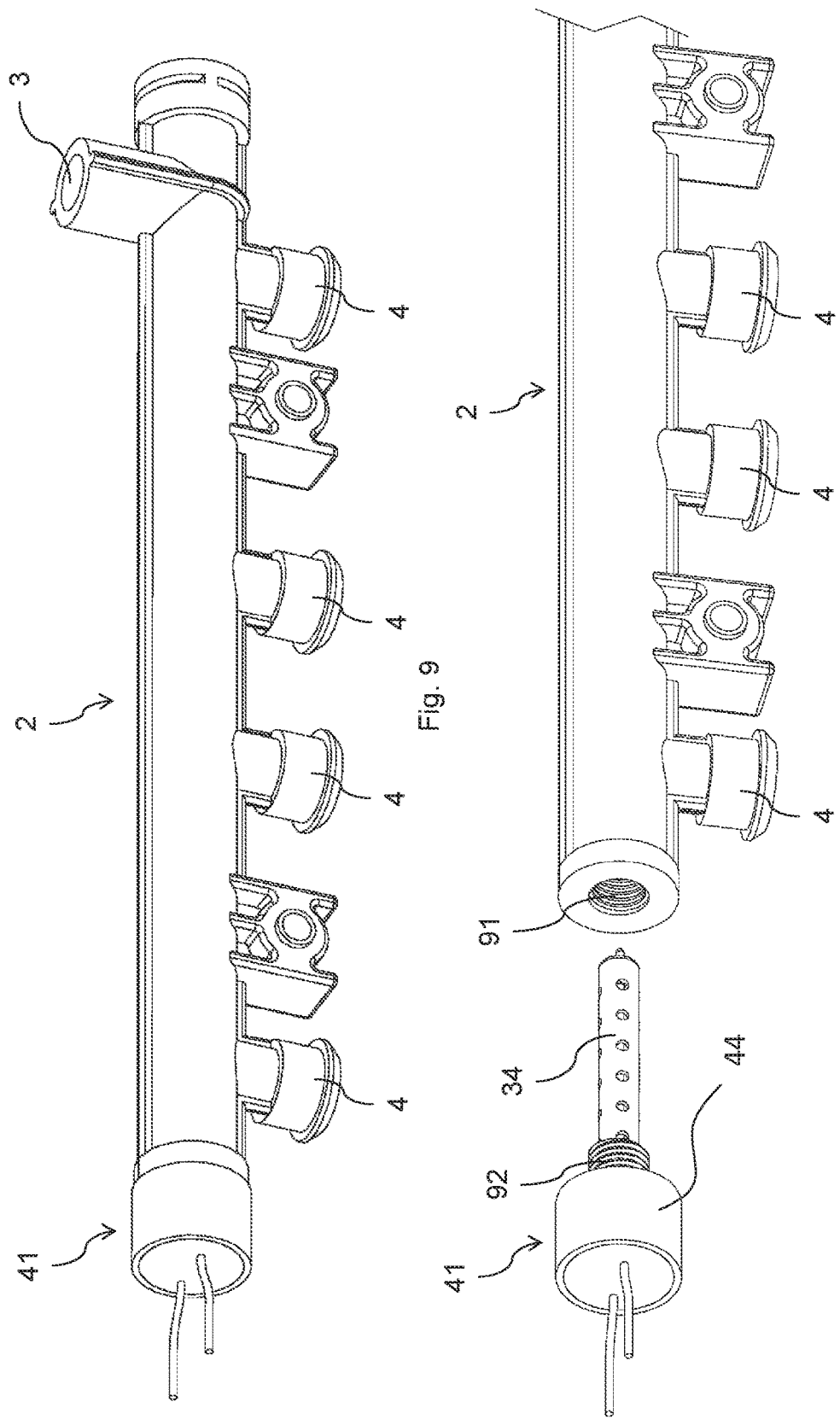

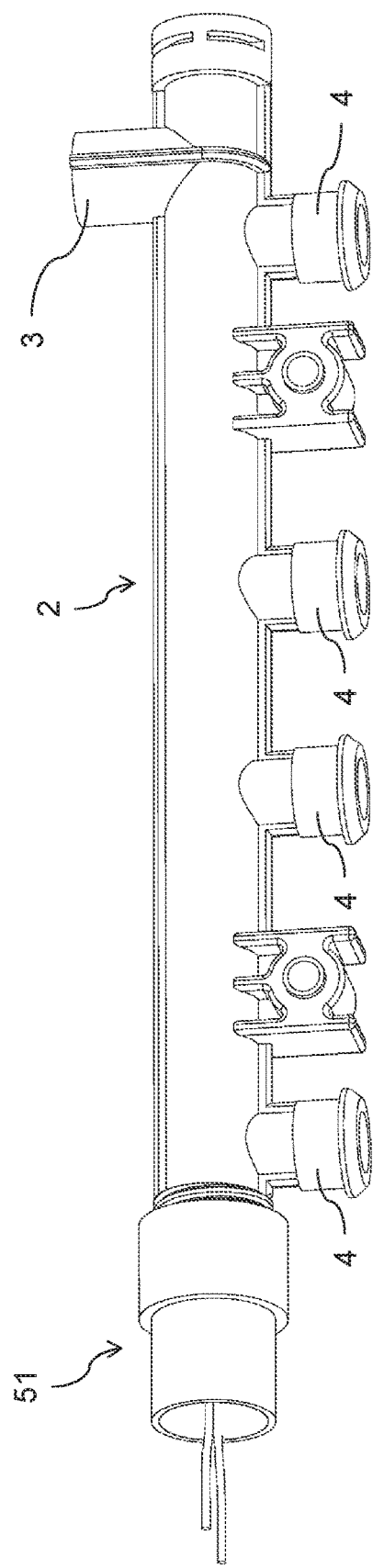
Fig. 11
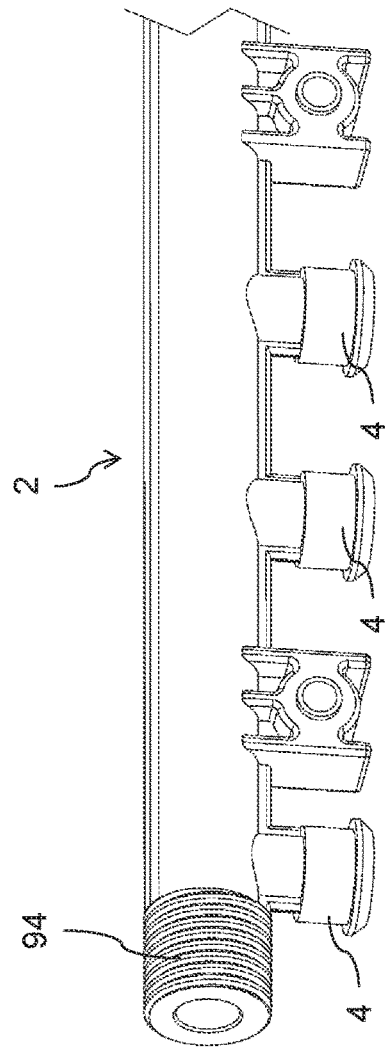
Fig. 12
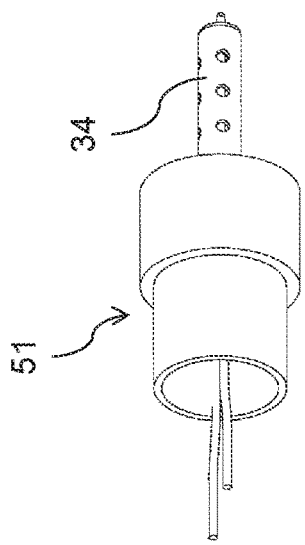

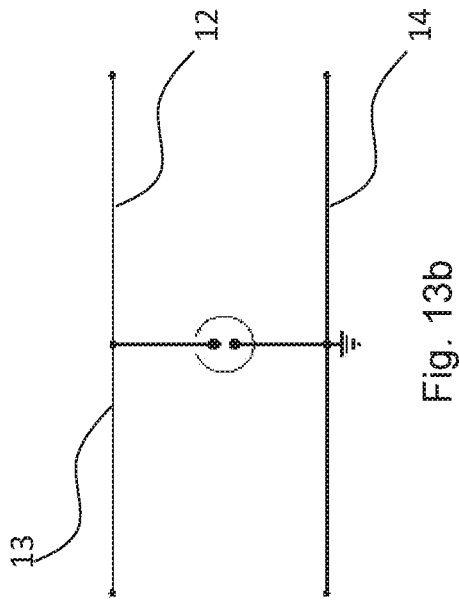
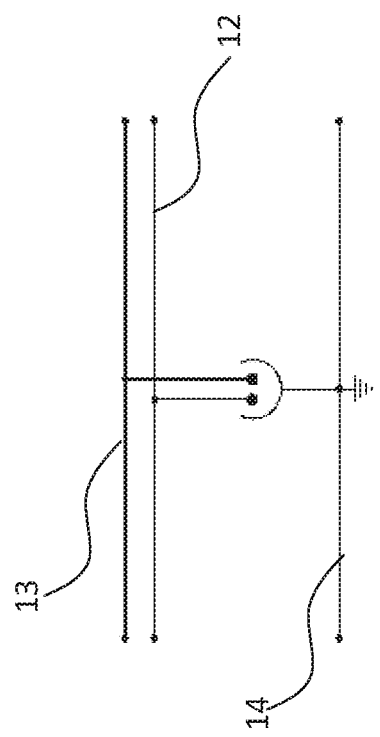
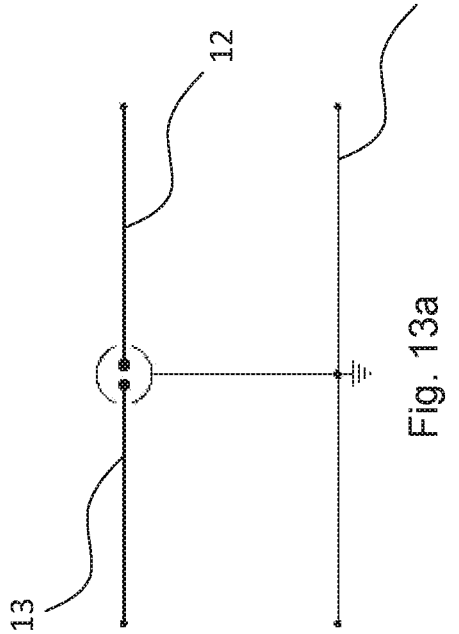

FLUIDS DETECTION SENSOR AND RAIL, IN PARTICULAR FOR AUTOMOTIVE FUELS

BACKGROUND OF THE INVENTION

1. Field of the Invention

The present invention relates to a sensor and/or a method for detecting the properties of a liquid, such as the presence and concentration of certain elements.

Preferably, the liquid is a fuel, such as a hydrocarbon or an alcohol or a mixture of hydrocarbons and/or an ethanol-containing mixture, and is designed to be supplied to an internal combustion engine, particularly for automotive use.

2. Present State of the Art

Electrochemical properties of a general fluid, particularly in highly electromagnetically polluted environments, are known to be difficult to measure, unless laboratory equipment is used.

Such equipment is complex and delicate and its practical use, e.g. in a vehicle such as a common car, is a hardly practicable and poorly competitive solution.

Furthermore, for electromagnetic compatibility, the detection process should not interfere with other equipment nearby, especially in vehicles.

A sensor for use in such kind of measurements is disclosed in U.S. Pat. No. 6,803,775, by Sanchez et al.

This sensor is housed in a fuel pressure regulator valve.

In the disclosed sensor, the fuel-contacting surface of the electrodes, which consist of conductors arranged along an outer armature conduit, has a maximized area, due to the provision of teeth on the inner surface of the conduit, for the sensor to have an appropriate transfer function for the type of liquid to be measured.

During normal operation, the sensor so disclosed is exposed to electromagnetic interference, which might affect the measurement process; this is because it is usually installed in the proximity of an interference source, such as a combustion engine.

Furthermore, such sensor is not suitable for operation with liquids having apparent changes of their electrical properties, as too large measurement errors would occur for high-conductance liquids, because the sensor would operate close to the lower limit of its measurement range, and would hence increase the detection error.

Also, in certain prior art solutions, such as the one disclosed in the U.S. Pat. No. 6,885,199, i.e. having an outer cylindrical electrode and a central wire-shaped or cylindrical electrode, the facing electrodes must be spaced apart to a given extent, to allow fluid to flow therebetween with no dirt build-up; nevertheless, a large spacing would negatively affect the dielectric, and hence the capacitance of the measuring capacitor and/or the measuring resistor.

In other words, with a given outside diameter of the sensor, if the radial distance between the electrodes is increased to facilitate the outflow of the liquid fuel and avoid dirt build-up, then the properties of the sensor will be changed, with detections switching from capacitive to resistive types (or vice versa): this may have a detrimental effect especially if the sensor is designed for dynamic sensing, i.e. for use on a moving fuel flow.

Similar considerations may apply, mutatis mutandis, to sensors designed for large tanks or rails, as described in the U.S. Pat. No. 6,842,017, in which the liquid stagnates in a chamber associated with the electrodes.

SUMMARY OF THE INVENTION

The present invention has the object to solve these and other problems by providing a method and/or a device for determining the characteristics of a liquid, such as its chemical, physical, electrical, electromagnetic properties, its composition, etc., which is designed particularly but without limitation for internal combustion engine fuels and mixtures thereof, and affords reliable detection even under changing operating conditions.

A further object is to provide a sensor that ensures accuracy and reliability in determining the characteristics of a flowing or moving liquid or fuel, such as a fluid or fuel circulating in a conduit or in the body of a hydraulic device, particularly a conduit or a body having a flow cross sectional area of less than 2 $cm^2$, or with a diameter of less than 16 mm.

Another object is to provide a device and/or a method for improving detection and/or measurement conditions, and particularly affording a greater measurement sensitivity, while avoiding abnormal conditions, such as dirt build-up and/or reduction of the flow that contacts the sensor.

Yet another object is to provide a method and/or a device that allows detection to occur by the emission of a frequency or voltage/current variable signal that can perform impedance and/or purely resistive measurements.

The invention further relates to a sensor for detecting fuel properties and/or a fuel rail to which the sensor may be mounted.

The main features of the invention are listed in the following claims.

BRIEF DESCRIPTION OF THE DRAWINGS

These and other features, resulting effects and advantages of the present invention will become more apparent from the description of a few exemplary embodiments as shown in the accompanying drawings, which are only given by way of non-limiting example, in which:

FIG. 8 is an exploded perspective view of the second embodiment of the sensor;

FIG. 9 is a perspective view of a third embodiment of the sensor of the invention, mounted in a fuel supply rail;

FIG. 10 is a perspective view of the sensor of FIG. 9, separate from the supply rail;

FIG. 11 is a perspective view of a fourth embodiment of a sensor of the invention, mounted in a fuel supply rail;

FIG. 12 is a perspective view of the sensor of FIG. 11, separate from the supply rail;

FIGS. 13*a*, 13*b*, 13*c* are respective wiring diagrams for the electrodes of the sensor of the invention.

DETAILED DESCRIPTION OF THE PREFERRED EMBODIMENTS

Figure 1:
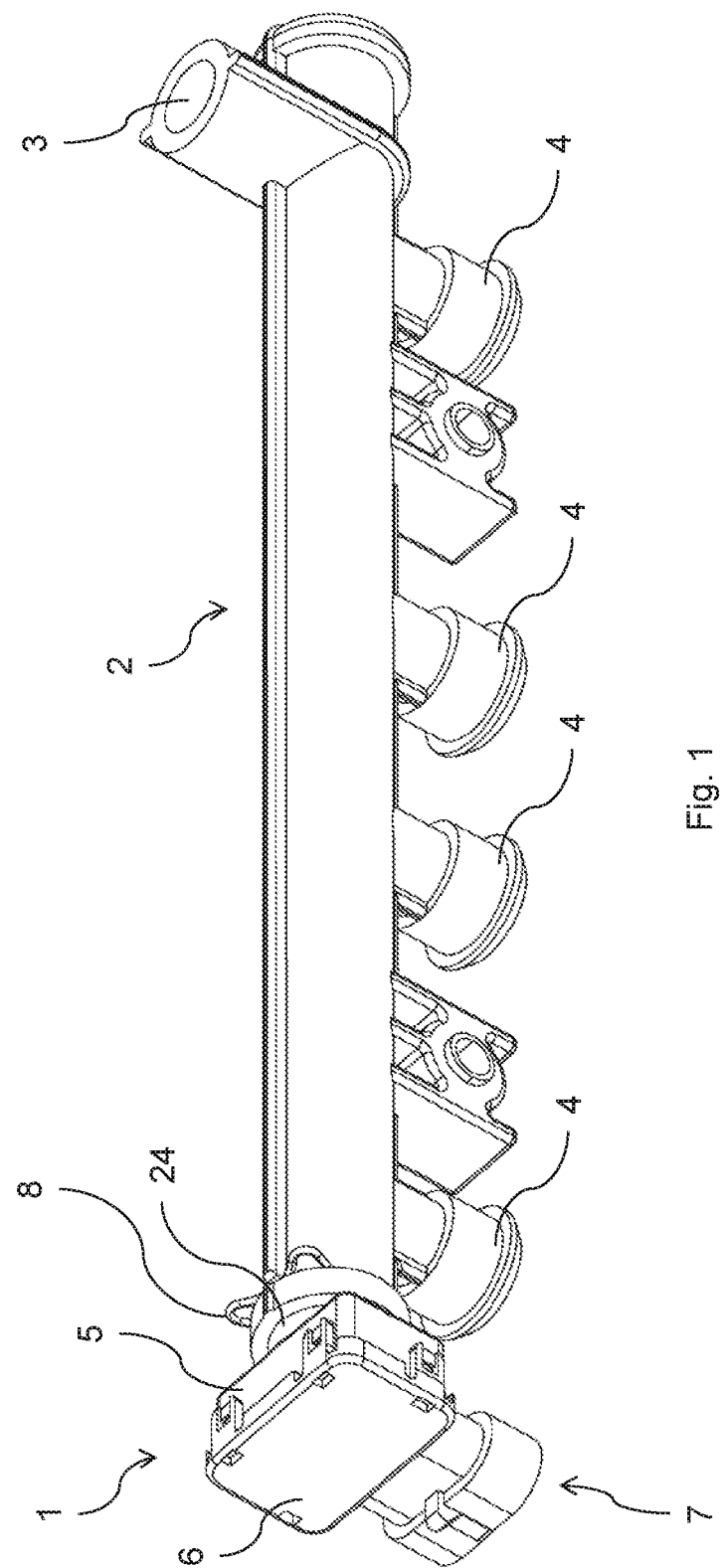
FIG. 1 is a perspective view of the sensor of the present invention, which is mounted to a fuel supply rail for an internal combustion engine.

Referring to the above drawings, and particularly to FIGS. 1 to 5, the present invention will be disclosed below with reference to a sensor 1 for detecting chemical and physical properties (e.g. electrical conductivity, dielectric strength, presence and/or concentration of substances, etc.) of a fluid, which is preferably mounted, in operation, in a fuel supply rail 2 of an internal combustion engine.

The sensor 1 of the invention is preferably suited for use with a fuel rail or a common rail, i.e. a pipe that delivers fuel (gasoline, ethanol, diesel oil, etc.) to the injectors in the engine. For this purpose, at least part of the sensor 1, preferably the entire detection part, is installed in an appropriate housing 24 of the supply rail 2, which has one fuel inlet 3 and fuel outlets 4.

The outlets 4 supply respective injectors and/or cylinders of an internal combustion engine, preferably of flexible fuel type, i.e. adapted to be supplied with various fuels, such as gasoline or ethanol or mixtures thereof, with an ethanol percentage preferably ranging from 25% to 92%.

While four outlets are provided in the supply rail 2 of the illustrated example, their number may change according to the number of cylinders of the combustion engine or else; the number of inlets of the supply rail may be also different from that in the figure, such as two or more inlets.

The sensor 1 also includes a part inserted in the housing 24 of the rail 2, which is designed to contact the liquid whose properties are to be detected.

Such inner part of the sensor comprises a pair of preferably axial inner electrodes 12 and 13, at least partially circumscribed by a preferably cylindrical or slightly frustoconical outer electrode 14, e.g. made of a sheet wrapped into such cylinder, which electrodes 12 and 13 are supported at their bases by a support element 15, such as a centering bush 15 made of an electrical insulating material. Such outer electrode 14, which preferably operates as a shielding element, particularly against electric noise, might also have another shape, such as a polygonal section shape and/or have either a closed profile or a partially open profile, e.g. a C-profile.

The electrodes 12, 13 and 14 and the sensor part inside the rail 2 will be described in greater detail hereinafter.

As shown in the drawings, the sensor 1 has a part external to the rail 2, which comprises an enclosure 5 for circuit components, to be described in greater detail hereinafter, which enclosure is closed by a lid 6; the external part of the sensor is further connected to the power supply and/or the network and/or the control circuit that controls the operation of the motor vehicle, via a three-pole connector 7.

Figure 2:
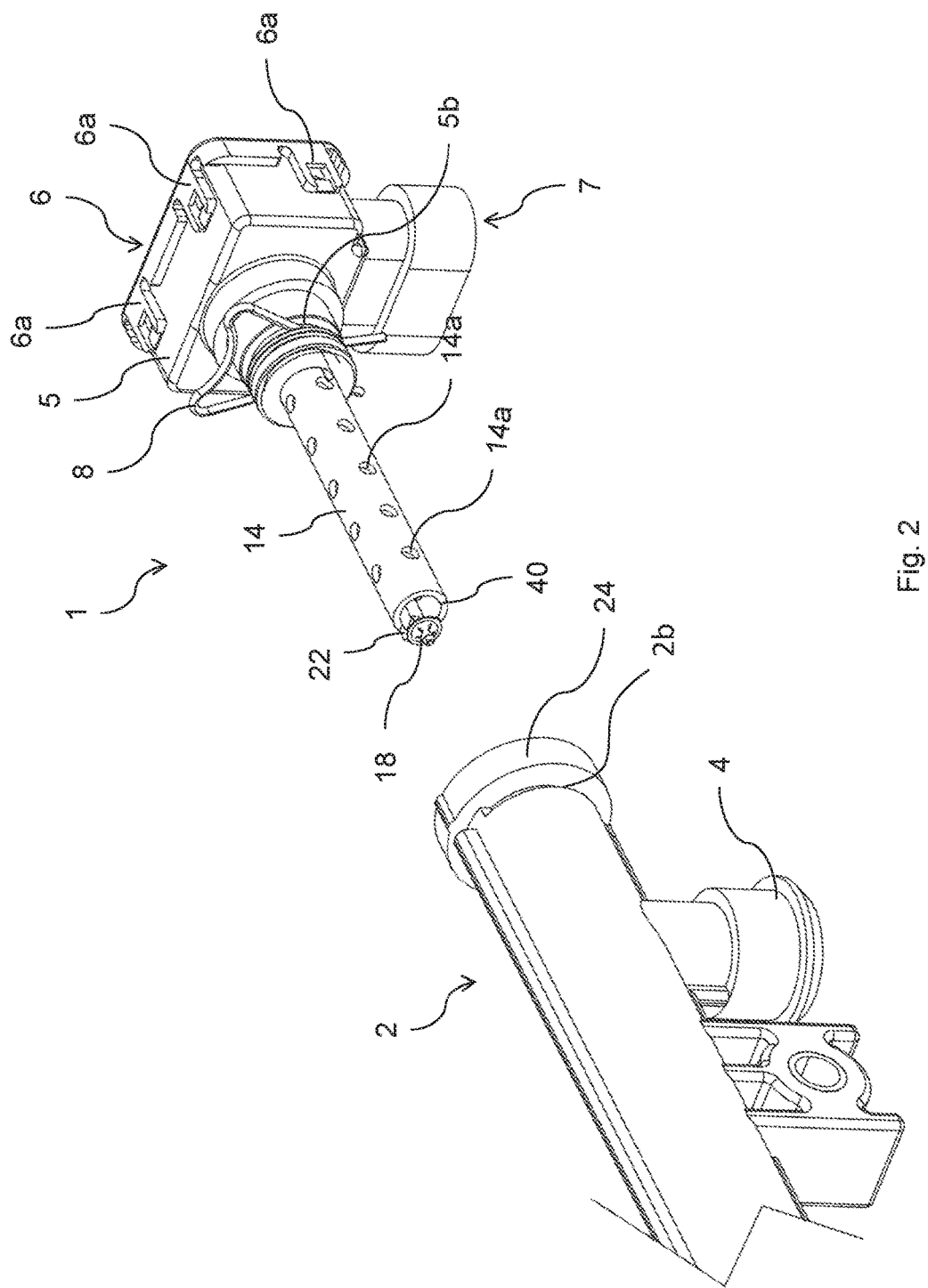
FIG. 2 is a perspective view of the sensor of FIG. 1, proximate to an end of the supply rail.
Figure 3:
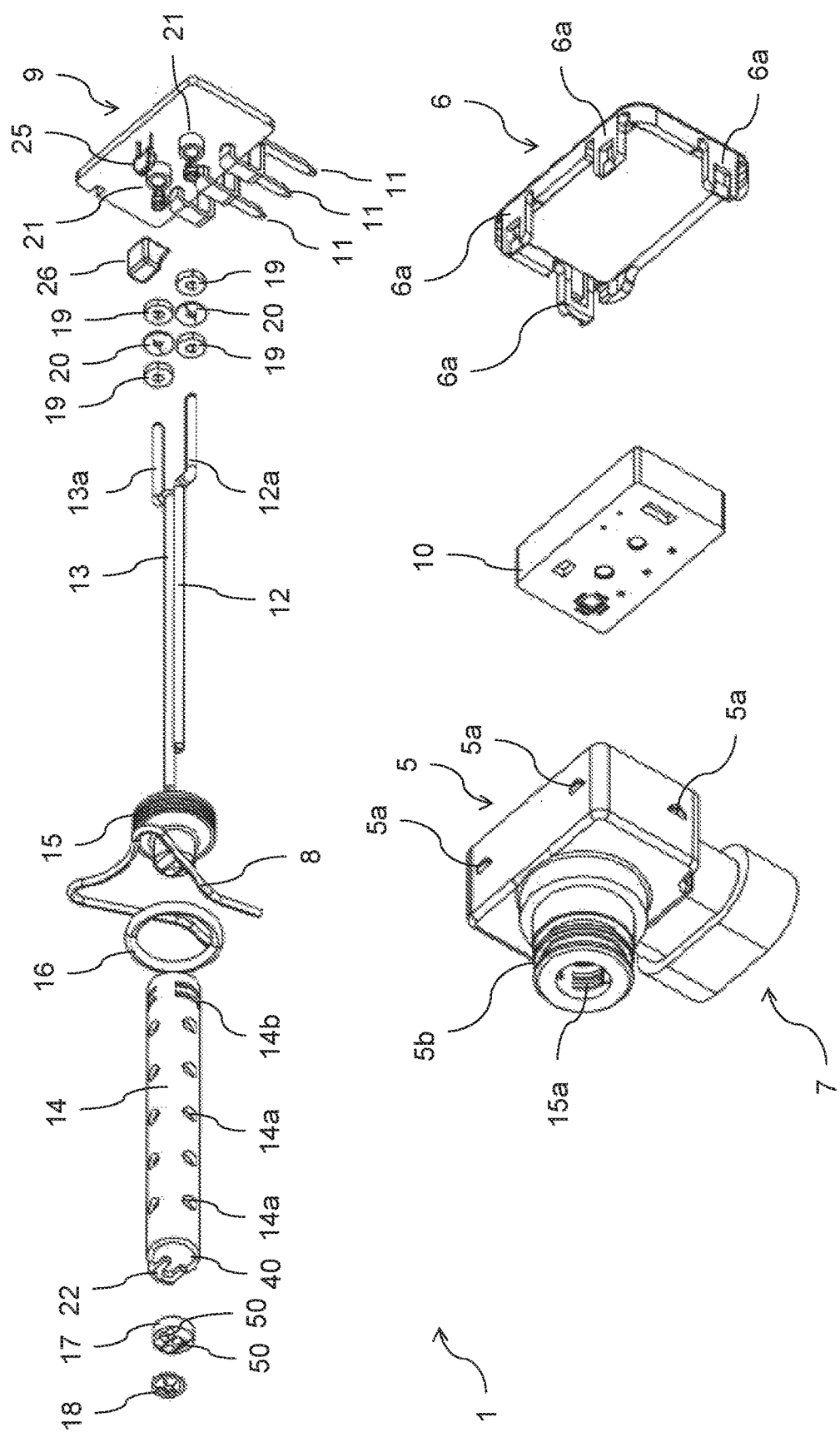
FIG. 3 is an exploded perspective view of the sensor of the present invention.

FIGS. 2 and 3 show that the enclosure 5 of the sensor is shaped to contain an electronic board or control circuit 9 and an insulating element or material 10 associated therewith.

The latter may be advantageously obtained by casting resin into the enclosure 5, to impart fluid-tightness thereto; this will appropriately seal the circuit 9, the various electronic components and the electrodes 12, 13 and 14.

The enclosure 5 and/or the lid 6 may possibly comprise electrically conductive parts, particularly having noise shielding purposes, which are made of metal or an electrically conductive polymer.

The board or circuit 9 has at least the purpose of detecting the properties and/or the state of the fluid, by means of electrodes; the latter are controlled or anyway used to perform measurements as explained below.

The circuit 9 also preferably has the purpose of converting such detected properties and/or states into data and/or values and/or signals of appropriate format. These signals and/or values and/or data are sent or transmitted to one or more of the terminals 11 of the connector 7 and/or to the further external circuit for controlling the vehicle having the sensor mounted thereto. The operation of the electronic board 9 and its components will be described in greater detail hereinafter.

In the example herein, the lid 6 closes the enclosure 5 of the sensor, to which it is secured by the appendages 6a, which engage in corresponding projections 5a of the enclosure 5; since the enclosure 5 and the lid 6 are formed of plastic or polymeric material, these parts can be easily closed with the appendages 6a and the projections 5a: any other solution to form the enclosure and/or the lid and/or to securely close the enclosure 5 by the lid may be obviously envisaged.

Furthermore, the enclosure 5 of the sensor and the lid 6 may also comprise seal means and/or undergo a welding and/or sealing process using resins or plastic films, or have appropriate means to assist protection of the whole system from external agents, such as dust, moisture or else.

As mentioned above, in this example the connector unit 7 is a three-pole male connector, having three contacts 11 that can be used for various functions, e.g. ground, power supply, fuel detection signal, where such ground terminal may be a terminal having a reference electric potential, such as a common electric potential for power supply to the circuit and for the detected and/or processed signal.

Obviously, as required by design and/or installation, the skilled person may appropriately assign functions to the connectors and/or set a different number of connectors or terminals.

As shown in the drawings, the connector unit 7 is also conveniently shaped for accommodating and/or connecting with a female connector (not shown), such as the female connector of external cables and/or said external circuit: as required by design and/or installation, the skilled person may select the most appropriate connectors for the purpose.

The support and/or centering bush 15 is associated with the enclosure 5 that has a seal 16 mounted thereto, which seal ensures fluid-tightness to the body of the enclosure 5 and prevents leakage of liquid, such as gasoline or ethanol from the rail 2 to the outside.

The support and/or centering bush 15 is preferably formed by molding of a thermoplastic material, such as co-molding or overmolding with the electrodes 12, 13, 14; particularly to obtain a semiprocessed product in which the electrodes are held in a stable position. Then, the enclosure 5 is preferably formed, by further molding of a thermoplastic material, such co-molding or overmolding with the bush 15 and the electrodes 12, 13, 14.

The materials and/or shapes of the bush 15 and the enclosure 5 are preferably selected to ensure fluid-tight coupling therebetween, preferably by at least partially melting or structurally bonding together, at least at their contact area; preferably, the bush 15 and the housing 5 are formed with a thermoplastic material or a polypropylene (PP) polymer, with the addition of a reinforcing filler, such as fiberglass (GF), particularly 30% filler or fiberglass with respect to the polymer or polypropylene. Preferably, the rail 2 is also formed with a thermoplastic material or a polypropylene (PP) polymer, with the addition of a reinforcing filler, such as fiberglass (GF), particularly 30% filler or fiberglass with respect to the polymer or polypropylene.

The rail 2 and the enclosure 5 are preferably adapted to be coupled together in a fluid-tight manner, preferably by welding or hot remelting of at least one of their respective parts, such as by laser or vibration welding; particularly by structurally and/or fluid-tightly bonding together, at least at their contact area, such as the area of the housing 24 of the rail 2.

The example of FIGS. 2-5 shows that the external electrode 14 has at its end a fork-shaped tip 22, through which the free end of the longer internal electrode (here the electrode referenced 13) extends and/or is coupled; with the sensor 1 in the assembled state, the tip 22 is interposed between a positioning element 17, such as an insulating element or disk, accommodated in the electrode 14 and a stop washer 18, such that the internal electrode 13 is stably associated with and/or positioned relative to the external electrode 14; in this configuration, both the internal 13 and external 14 electrodes are, for instance, electrically connected to a reference potential or ground.

The electrodes 12 and 13 are arranged side by side, at least over most of their length within the external electrode 14, along the longitudinal axis of the latter.

For this purpose the insulating disk 17 supports at least the end portion of the shorter electrode 12 and acts as an intermediate rest for the longer electrode 13.

On the other hand, the base end 12a, 13a of the internal electrodes 12, 13 is bent, for instance, at right angles into a fork, i.e. a section along which the internal electrodes are spaced at a longer distance, with the tines or end terminals 12a and 13a engaging in respective female electric clamps 21 in the board 9.

Therefore, the clamps 21 ensure electric contact of the electrodes 12, 13 with the circuit associated with the board 9. Support and/or rest rings 19 and O-rings or seal elements 20 are provided on the base ends 12a, 13a; such rings 19 being preferably adapted to laterally retain said seal element 20, thereby improving its radial sealing action.

The electrodes 12 and 13 are wire- or bar-shaped conductors, particularly formed as cylindrical bars of metal or any other appropriate electrically conductive material, and are preferably made of a material or metal resistant to corrosion and/or electrochemical reactions, such as steel or noble metals or electrically conductive alloys or polymers.

During operation of the sensor, the electrodes 12 and 13 directly contact the liquid fuel that flows in the rail 2: this allows resistive and/or capacitive detection and/or both by the sensor, according to a possible teaching of the invention.

It shall be noted that, to fulfill at least one teaching of the invention, the length and thickness of the electrodes 12 and 13, the spacing (i.e. the distance) therebetween and their material, in combination with other elements, such as the external electrode 14, help to define the transfer function or at least one characteristic of the sensor 1, and preferably adapt it to the target liquid.

For instance, if the liquid has a high electrical conductance, the two electrodes 12, 13 shall be preferably spaced apart; conversely, if the conductance of the liquid is low, the distance between two electrodes 12, 13 shall be preferably reduced.

The same applies to the permittivity; for instance, if the liquid has a low permittivity, the electrodes should be at a short distance, otherwise they should be further spaced apart.

Assuming an equal characteristic of transfer function, the distance between the electrodes is proportional to the conductance and/or the permittivity of the liquid to be measured.

The electronic board 9 is mounted in the enclosure 5 to be located at the front, to allow connection of the electrodes 12 and 13 with the clamps 21.

As mentioned above, the electrodes 12 and 13 extend at least over part of their length in an external electrode 14, which preferably has a substantially tubular or frustoconical shape, and is open at least at one end and/or along one side; the electrode 14 preferably has a closed cylindrical cross-section, but may also have a polygonal or other (e.g. lobed) cross-section, possibly open at one point.

This electrode 14 comprises an electrically conductive metal cylindrical wall, which is perforated and/or partially open to allow the liquid fuel to flow therein; here, the holes or apertures 14a have a circular shape, but they may also have different shapes, e.g. a rectangular or slot-like shape. Furthermore, the apertures may also extend in a circumferential, helical and/or curvilinear fashion, in addition to the axial extension as shown in the drawings, to facilitate liquid flow to and from the interior of the sensor.

Figure 4:
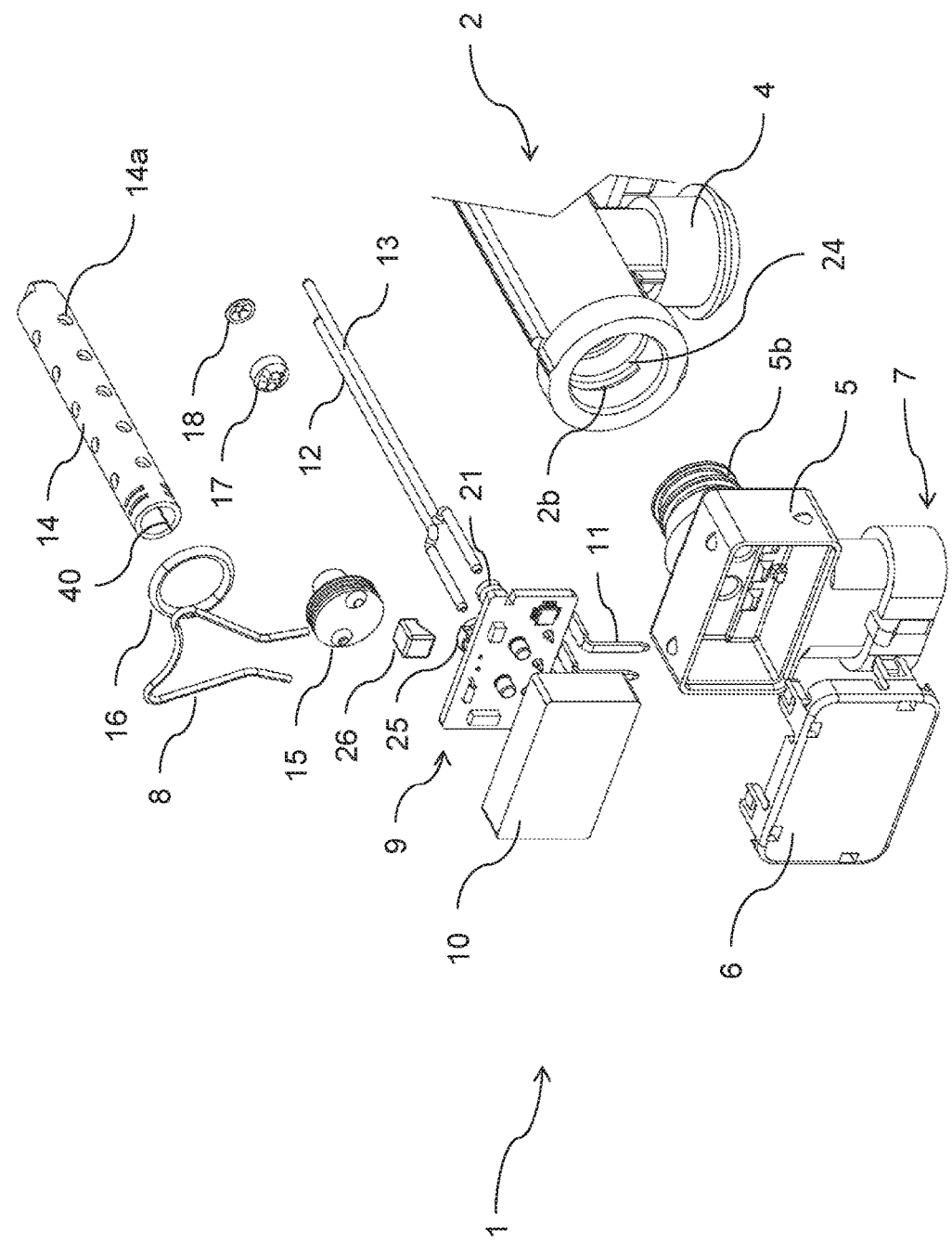
FIG. 4 is an exploded perspective view of the sensor of the present invention, as taken from the side opposite to the previous figure.

As shown in FIG. 4, the electrode 14 also has an axial cut or aperture 40 extending along said cylindrical wall; such aperture, e.g. consisting of the juxtaposed area of the two ends of a bent sheet, may facilitate the flow of fluid or fuel therein, i.e. towards the internal electrodes 12 and 13.

The holes and/or apertures may be generally provided in various numbers and shapes, to better adapt the performances of the sensor to the type of liquid whose properties have to be detected; nevertheless, the distinctive feature of the electrode 14 shall preferably be the arrangement of apertures along its longitudinal extension, in view of ensuring axial flow of fuel within the sensor.

Therefore, these holes or apertures 14a and/or the shape of the electrode 14 shall be designed to facilitate the flow of fluid in the electrode 14, and particularly the flow in the internal electrodes 12 and 13.

It shall be noted herein that the distal end of the sensor is open to allow the passage of liquid. The base end of the external electrode 14 partially fits into the centering bush 15; on the other hand the enclosure 5 of the sensor is secured to the rail 2 by means of a clip 8, here an elastic wire fork, and the O-ring 16 ensures a sealing action therefor.

For this purpose, a groove 5b is formed in the front side of the enclosure 5, i.e. the one to be fitted into the rail 2, which groove is aligned with a slit 2b in the rail 2, which is engaged by the clip 8, with the sensor in the assembled state.

According to a preferred embodiment, slits 14b,15b are formed at the base end of the external electrode 14 and on the wall of the centering bush 15, to allow penetration of the molding material, i.e. for better fixation of the external electrode 14 to the enclosure 5.

In this exemplary embodiment of the invention, the longer internal electrode 13 is electrically connected with the external shielding electrode 14, and both are at the same electric potential.

The electrodes 12 and 13 are preferably spaced apart from each other and/or from the sensor 14 by means of an insulating element or disc 17, which is substantially secured in the electrode 14 and has ports 50 allowing axial outflow of the liquid fuel; such insulating element 17 may be also omitted or have a shape that does not hinder fluid flow.

A support 17, preferably mounted to one end of the electrodes 12,13, is preferable to prevent the latter from being moved toward and away from each other, as a result of the pressure exerted by the motion of the liquid in which they are immersed: these effects or movements might change the transfer function of the sensor and make detection difficult.

In this exemplary embodiment, the sensor 1 also senses the temperature of the fluid in contact therewith; for this purpose the electronic board 9 is fitted with a temperature probe 25, preferably associated with a material or enclosure 26, such as a thermally conductive material, resin or gel, i.e. adapted to improve heat transfer, which indirectly exchanges heat with the liquid fuel.

It shall be noted herein that the bases 12a e 13a of the electrodes 12 and 13 are not contacted by fluid, as they are overmolded, which means that the bases 12a and 13a of the electrodes 12 and 13 are preferably in contact with the enclosure 5 and/or the bush 15, and exchanges heat therewith; preferably such bases 12a and 13a of the electrodes 12 and 13 are proximate to and/or in contact with said probe 25, for improved temperature sensing.

Therefore, the sensor 25 indirectly senses temperature, for example through heating of the electrodes 12 and 13 and/or the enclosure 5 and/or the bush 15.

Assuming that no sudden temperature changes occur in the liquid, the position of the temperature probe or sensor 25 allows the latter to provide a value that is adequately indicative of the temperature of the liquid to be measured. The sensor may be of either active type (e.g. a thermocouple), or of passive type (e.g. a thermistor) or else.

Obviously, the skilled person may select the temperature sensor and its position as appropriate for optimized fulfillment of design and/or installation requirements.

Figure 5:
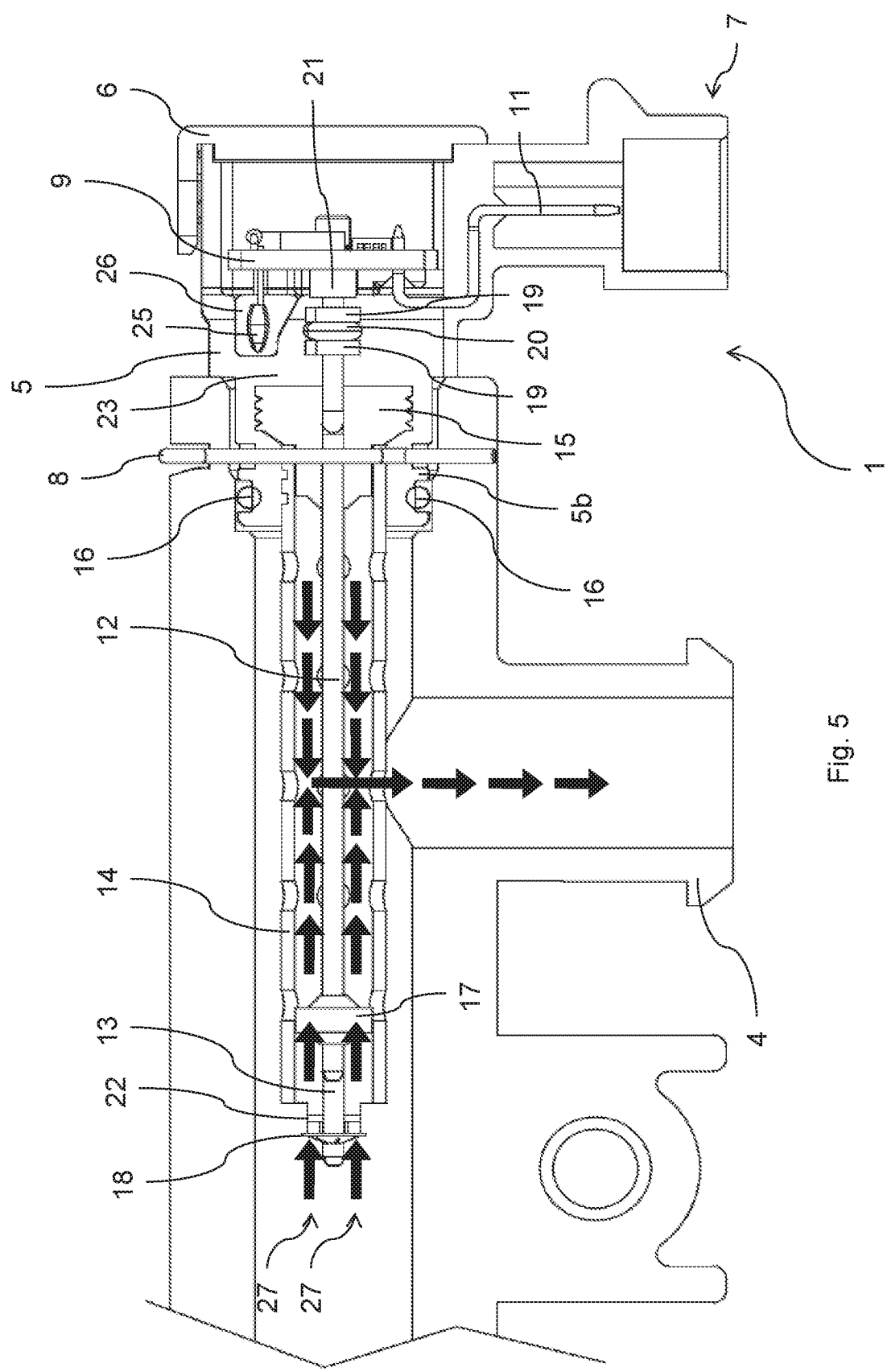
FIG. 5 is a longitudinal sectional view of the sensor of the present invention, mounted to an end of the supply rail.

FIG. 5 shows that the main flow 27 of the liquid fuel to be measured impinges upon the sensor before reaching the outlet 4.

During operation of the sensor 1, i.e. when the latter senses the properties of the liquid in the rail 2, the part of the sensor 1 with the electrodes 12, 13 and 14 is accommodated in the rail 2 and hence immersed in this liquid.

The detected electric signal, e.g. obtained by applying an alternating potential difference to the ends of the internal electrodes 12, 13 and/or the external electrode 14, provides an indication about the properties of the fluid or liquid fuel, such as the fluid contained in the rail 2.

Particularly, in the case of gasoline, ethanol and mixtures thereof, the sensor can provide an accurate indication of any change of the operating state of the system.

For instance, the presence of variable amounts of additives in gasoline (e.g. antiknock agents, solvents, etc.), or water in ethanol causes changes in the electrochemical properties of the liquid, such as its conductance (i.e. the inverse of resistance).

The sensor of the invention can detect such changes of the electrochemical properties of the liquid; for instance according to a change in the signal, such as a change in the electric voltage or current circulating in the circuit associated with the board 9, which change may be conveniently processed to provide an indication of fuel composition.

It shall be noted herein that the above mentioned advantageous effects may be obtained by operating with low frequency signals applied to the electrodes 12, 13 and 14, i.e. below 100 Hz, preferably below 50 Hz and more preferably ranging from 5 to 30 Hz.

This is because the sensor of the invention has been shown to have a surprisingly effective operation even with these frequency values.

This also prevents the generation of appreciable electromagnetic interference with electronic equipment located nearby; these and/or other characteristics allow the sensor of the invention to be particularly suited for association with devices and/or systems for supply fuel to internal combustion engines, which are known to usually have an electronically controlled operation.

Furthermore, the above described shape and arrangement of the electrodes 12, 13, and 14 and their connections impart a non-negligible inherent electrical capacitance to the fuel sensor 1.

This capacitance may be advantageously controlled to improve detection and/or reduce the electromagnetic noise captured by the sensor 1 and generated by external sources, which in automotive applications as is the case herein can also consist of the engine ignition and injection system.

An ignition system for an automotive combustion engine is known to generate electromagnetic emissions over a very wide spectrum, with frequencies ranging from 100 kHz' and 10 GHz.

According to the teaching of the invention, the sensor 1 may be schematically represented by an electric model comprising a resistor and a capacitor connected in parallel therewith.

Appropriate selection of the sizes, shapes and materials of the electrodes 12, 13 and 14, can provide a capacitance value of the capacitor ranging from 10 pF to 246 pF, and preferably from 91 pF to 165 pF. This value changes according to the liquid in which the electrodes 12, 13 and 14 are immersed.

The resistance value as measured at the ends of the electrode 12, 13 ranges from 1 kOhm to 503 kOhm, and preferably from 14 kOhm to 490 kOhm; this value also changes according to the liquid in which the electrodes 12, 13 and 14 are immersed.

Figure 6A:
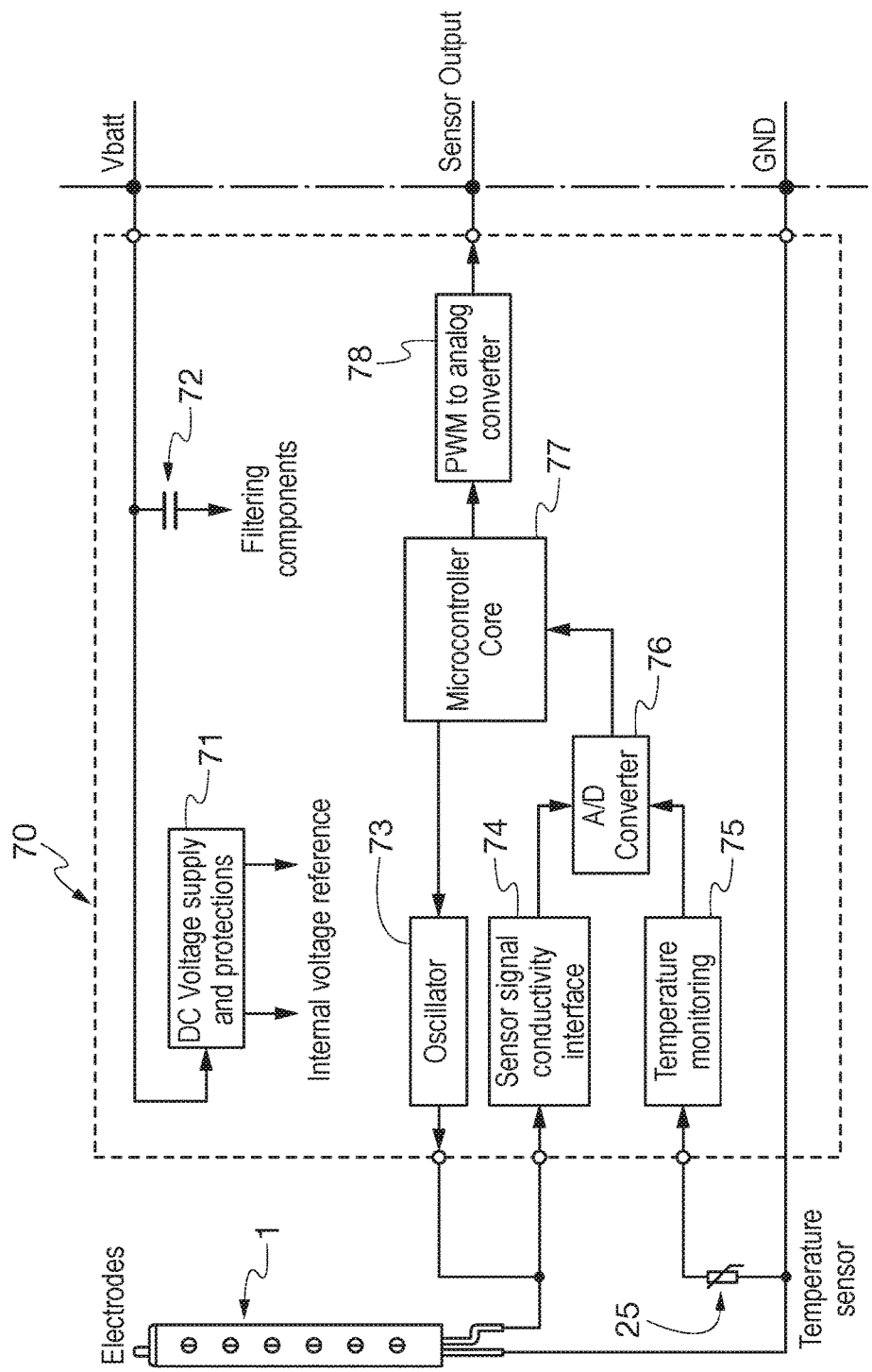
FIGS. 6*a*, 6*b*, 6*c* show the block diagrams of various embodiments of the circuit that is or can be associated with the sensor of the previous figures.
Figure 6B:
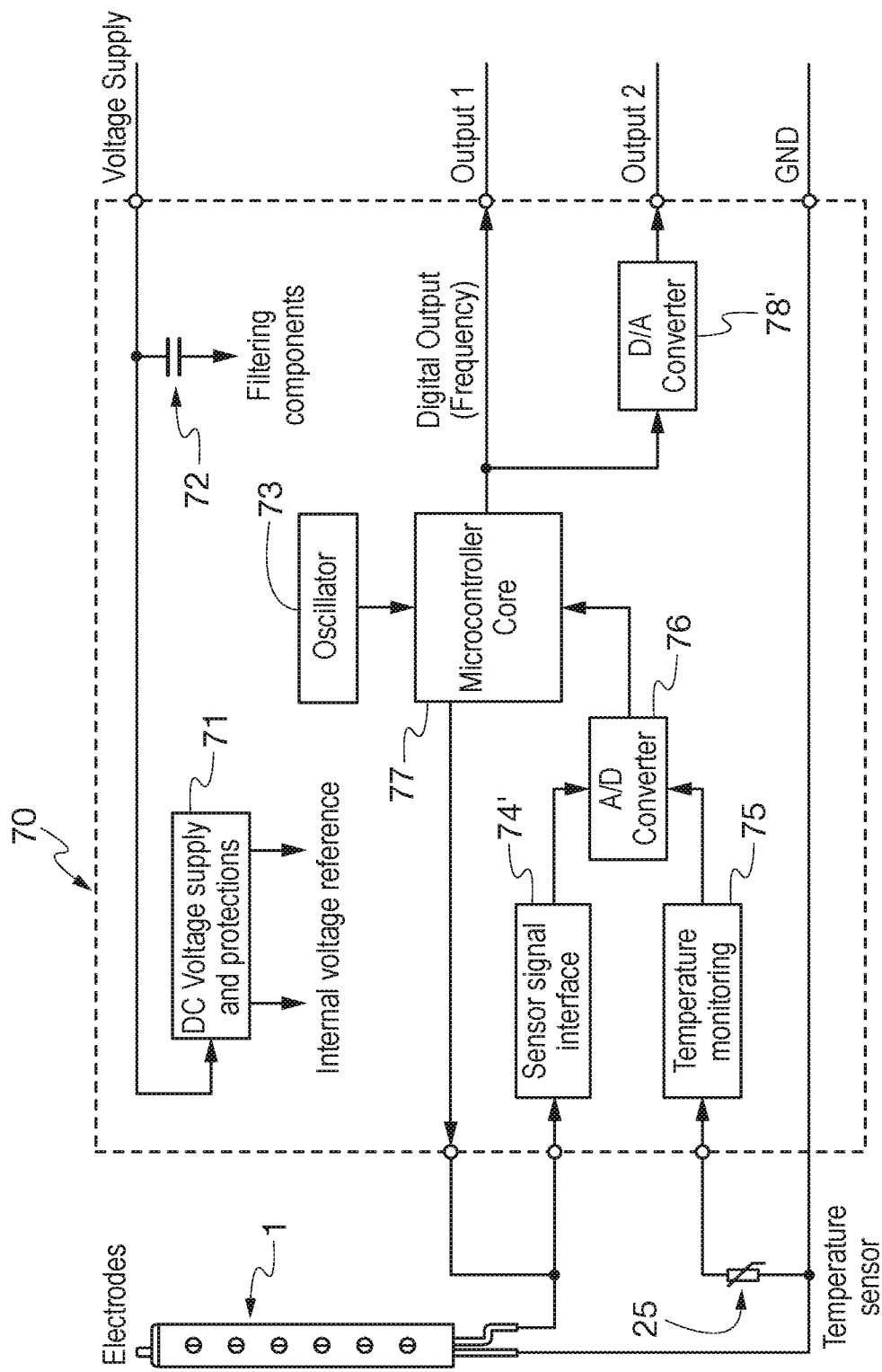

FIGS. 6a and 6b show a block diagram of a possible embodiment of the measuring and/or control electronics 70, which may be installed for instance on the electronic board 9 that is part of the sensor 1 or may be designed as an electronic circuit 70 or board 9 independent of the sensor 1.

The circuit 70 comprises at least some of these components: A stabilized voltage supply or generator 71; a power supply filter 72, which is used to reduce input noise to the circuit 70, an oscillator 73, an interface or circuit 74,74' for measuring a given magnitude of interest, such as impedance; an interface or circuit for measuring temperature 75, preferably sensed by the temperature sensor 25; an analog-to-digital signal converter 76, for converting input analog signals into a digital format; a microcontroller or logic control unit 77; a memory, which is possibly part of the microcontroller 77; a digital-to-analog signal converter, which is possibly part of the microcontroller 77; a frequency signal generator, which is possibly part of the microcontroller 77; a PWM (Pulse Width Modulation) to analog signal converter. The circuit 70 is powered by the stabilized voltage generator 71 (e.g. a voltage stabilizer, a battery, etc.), whose input current is filtered by the power supply filter 72, which is generally composed of passive electronic components, such as capacitors and resistors.

Figure 6C:
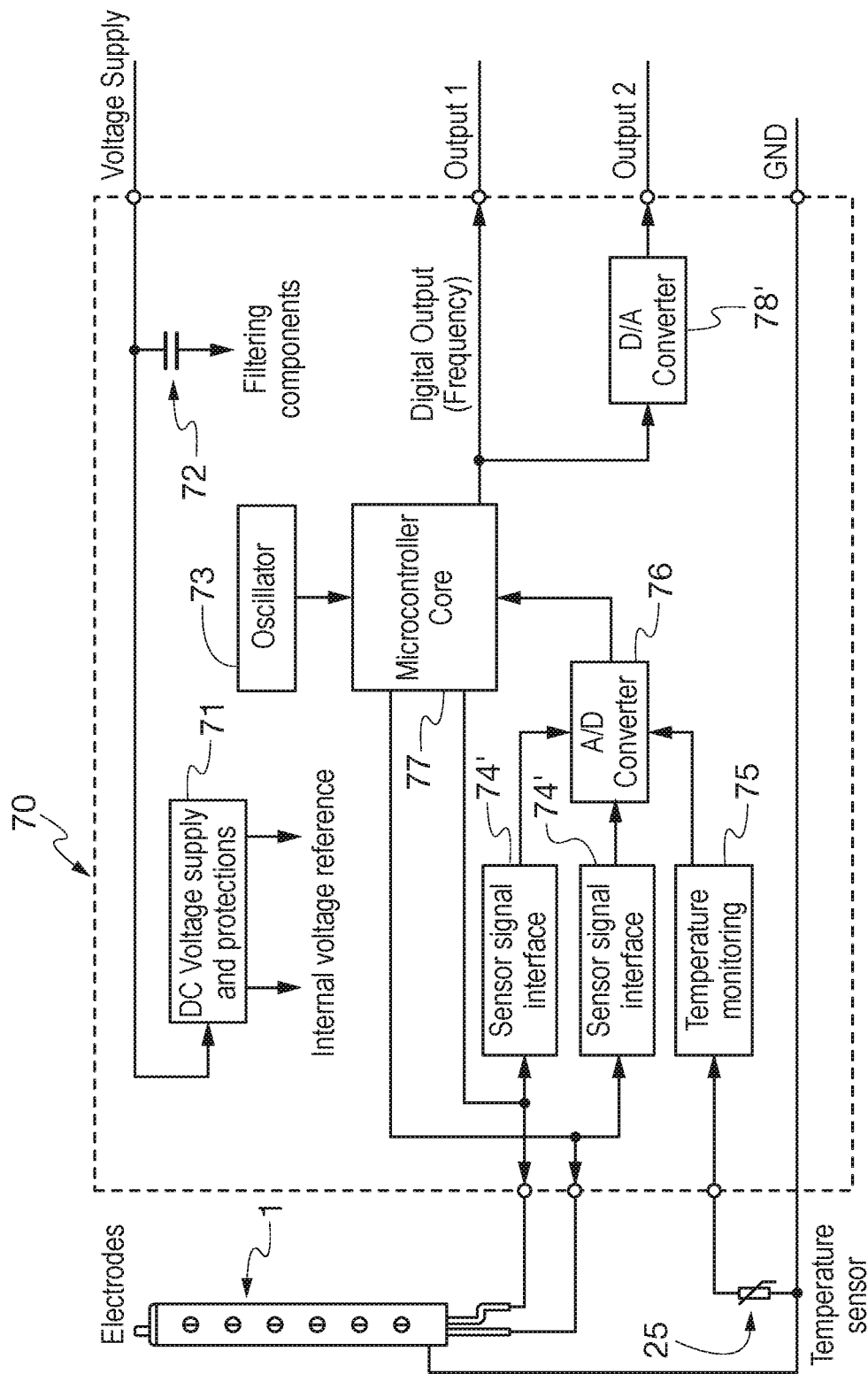

The circuit 70 is connected to the sensor 1, which is energized by the oscillator 73, and the output measurement signal of the sensor 1 is input to the interface 74,74' for measuring the magnitude of interest. As shown in FIG. 6c, two or more measuring interfaces 74' may be used, to perform two separate measurements, e.g. capacitive measurements, to increase the reliability of the measuring system, or to measure the magnitude of interest using two different measuring ranges, for advantageously extending the measuring range of the system while advantageously maintaining a low measurement error.

Figure 7:
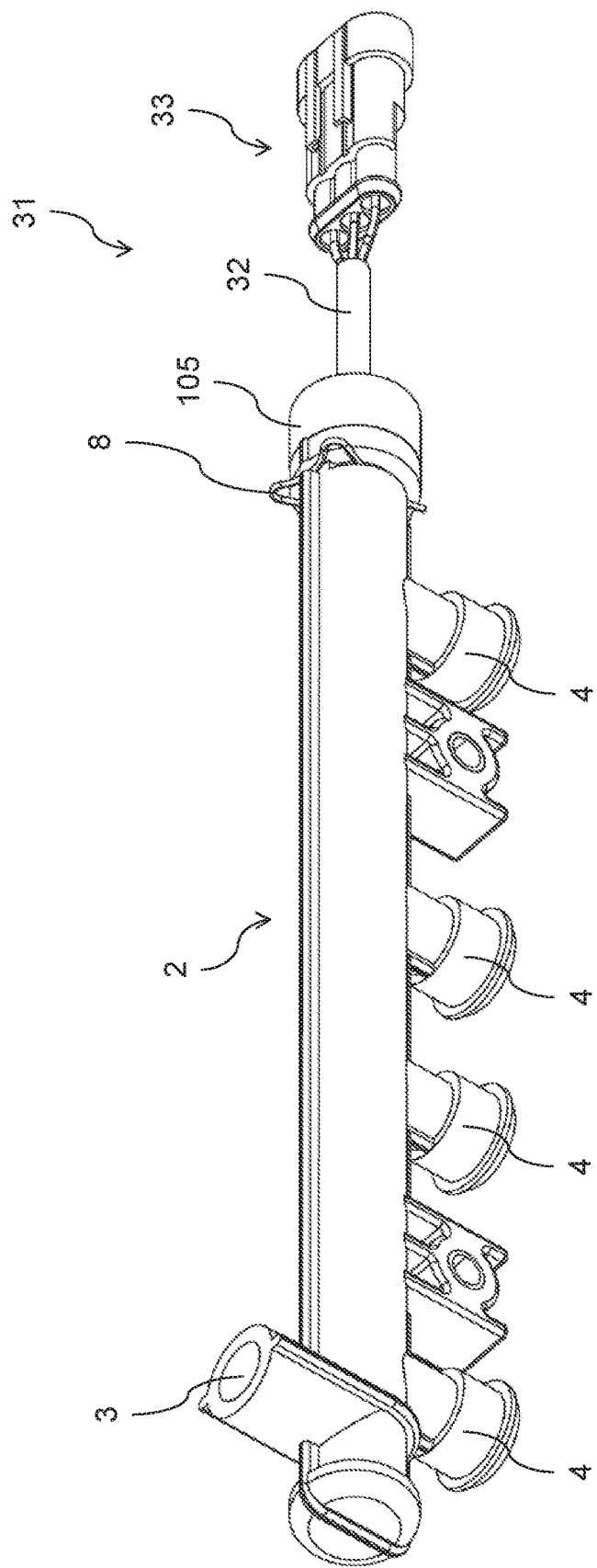
FIG. 7 is a perspective view of a second embodiment of the sensor of the invention, mounted in its supply rail.

More generally, the oscillator circuit 73 and the measuring circuit 74 may be connected either to one or more electrodes, or to one internal electrode, as shown in FIG. 6a, for a sensor equivalent to that of FIGS. 1-5, otherwise the oscillator circuit 73 and the measuring circuit 74 may be also connected to other internal electrodes, like in the case of the sensor of FIGS. 7-8, where these circuits may be also split, i.e. one for each electrode.

In FIG. [MB1] 6c the oscillator circuit 73 is part of the microcontroller 77, which microcontroller generates a frequency output to the sensor; here two separate outputs are also provided, one for a frequency signal and the other for an analog signal, which are connected to two respective terminals of a four-way connector, with the ground in common; in this configuration, the output signal may have a frequency that changes in proportion to the measured and/or processed value, as well as an output having a voltage that changes in proportion to the measured and/or processed value.

In order to allow measurement compensation using the temperature of the liquid to be measured, the output signal of the temperature sensor 25 is input to the temperature measuring interface 75.

Therefore, the interfaces 74 and 75 send the signal to the analog-to-digital converter 76, which converts the data as measured by the sensors 1 and 25 into a digital format that can be used by the microcontroller 77.

Then, the microcontroller 77 will implement an appropriate logic for appropriate detection and/or processing and/or compensation, also in view of making measurement independent of temperature by numerical compensation.

For this purpose, the memory means may advantageously store data useful for fluid sensing, such as reference data or data tables or data deriving from processing by the circuit 70, such as factory default data of the device 1 or data stored through later steps for testing, calibration or regulation of the sensor 1 and/or the external system with which the sensor 1 is associated.

Preferably, the memory means are of non-volatile and/or rewritable type, such as an EEPROM or Flash memory; such data is preferably written or stored by the circuit 70 and/or the microcontroller 77 and/or through a connection to terminals 11 of the connector 7.

Therefore, the detection method of the invention may include the following additional steps: sensing a temperature of the liquid; using the temperature value so sensed to compensate for the estimate of the value of the magnitude of the liquid, possibly storing such value of temperature and/or of the temperature-compensated magnitude.

Then, the result processed by the microcontroller 77 is provided at the output of the circuit 70, e.g. by PWM modulation, to the PWM-to-analog converter 78, which will provide the temperature-compensated measurement value at one of the pins 11 of the connector unit 11; particularly such signal value will have a frequency and/or pulse width proportional to at least one property of the fluid or fuel.

According to design and/or installation requirements, the skilled person may choose to use a different electronic circuit and/or the most appropriate measurement representation (e.g. voltage, current, etc.).

In one or more variants of the circuit of FIG. 6a, as shown in FIGS. 6b and 6c, the circuit may not include the PWM circuit 78, and the microcontroller circuit 77 may be connected to said pin 11, i.e. the circuit 70 may provide an output digital or analog signal proportional to the measured and/or processed value. In the latter case, the analog signal may be generated using a digital-to-analog converter 78'.

Further possible variants of the sensor may be obtained by changing the connection patterns of the electrodes 12, 13 and 14 in the circuit; a possible solution is obtained, for instance, by connecting the two central electrodes 12, 13 in series, and by maintaining the external electrode 14 independent, and connected to the ground (FIG. 13a).

Alternatively, the sensor may be connected in parallel, where one internal electrode 12 or 13 may be also connected to the ground, for a single detection (FIG. 13b); both internal electrodes 12,13 may be also connected to respective detection lines, for double measurements (FIG. 13c).

In terms of construction, it will be appreciated that the sensor 1 of the invention has a small size and may advantageously easily placed in the fuel rail, thereby affording a regular outflow of fuel to the outlets 4, as shown in FIG. 5, while providing optimized sensing performance and/or high sensitivity.

This is due to the particular structure of the sensor, which also has apertures 14a, 40 on the external electrode 14, which are arranged over most of its longitudinal extension, and to its distal end, which is also preferably open to allow the passage of the liquid fluid.

In addition to these features, the two internal electrodes 12 and 13 have a thin configuration, as they are formed as thin conductive bars.

Accordingly, it will be appreciated that these structural and functional feature of the sensor both allow it to have a thin profile and be also introduced in small-diameter rails, and facilitate axial outflow of fuel therein, without affecting its electric detection performance, in terms of both resistive and capacitive detection.

It shall be noted herein that the fluid may flow either continuously along the sensor, i.e. from one end to the other of the electrodes 12, 13, 14, or discontinuously, as shown in FIG. 5: in the former case, the flow follows a single path, in which the electrodes 12, 13, 14 are located, whereas in the latter case, there may be two opposed flows, following respective paths from the ends of the electrodes.

As shown in FIG. 5, the sensor of the invention is suitable for use both when there is a fluid outlet 4 adjacent to the sensor, and when the fuel flows along a path in which it contacts the sensor and flows on in a rail 2 towards another outlet.

It should be noted that, in both cases, the fluid path is preferably open along the reference direction defined by the electrodes 12, 13 and 14, whereby the fuel continuously flows without ever stagnating.

It should be added that, as used in this disclosure and the following claims, the term flow shall be intended in a broad sense, including turbulent flows, laminar flows or mixed flows. Therefore, the present invention also affords fuel sensing under dynamic conditions, and not only under static conditions, like in the prior art.

It shall be noted in this respect that, by changing the length and/or size of the electrodes 12, 13 and 14, the sensor may be adapted to the physical and chemical properties of the fluid and/or to its flow rate, velocity and other parameters as may be applicable from time to time. These and other features of the invention particularly prevent stagnation of fuel in the sensor, thereby avoiding any deposition of impurities or fouling thereon, which might affect operation and detection reliability with time.

The sensor may be possibly removed from the fuel rail 2 with which it is coupled by appropriate releasable means, such as the front part of the enclosure 5, to which it is secured by the clip 8, for instance for easy maintenance and/or testing and/or replacement.

In other words, the configuration of the sensor 1 allows removable installation thereof in a fuel rail 2.

The particular configuration of the sensor also allows it to be mounted to at least one end or a seat of the fuel rail, where fuel heaters, typically known as glow plugs, are usually located. The applications of the sensor of the invention are thus increased, as shown by the number of possible variants of the above example, some of which will be described below with reference to relevant parts other than those mentioned above, for purposes of brevity.

When possible, the same numerals will be used to designate parts that are structurally or functionally equivalent to those illustrated above, whose description will be found above, for purposes of brevity; therefore, at least part of the above description may be deemed to be also incorporated in the following examples.

A first variant, as shown in FIGS. 7 and 8, consists of a sensor 31 where the measuring electronics is omitted, i.e. where the circuit 70 may be external to the sensor device 1.

As shown, in this case there is an enclosure 105, substantially corresponding to the previous enclosure 5, which also incorporates the electrode centering bush; the body 105 partially fits into the end of the fuel rail 2.

A three-pole cable 32 connects a connector unit 33 to the electric contacts of an external electrode 34 (whose shapes and/or functions are similar to those of the external electrode 14, without the tip 22).

The electrode 34 accommodates the insulating support element 17 and the additional support 35 for the internal electrodes 12,13; while these insulating elements are shown for simplicity as disk-shaped elements, they may have another shape, particularly suitable to allow circulation of the flow on the electrodes. A contact element 36 is fitted around the base of the external electrode 34, with one end 36a forming, with the bent ends 12a,13a of the electrodes, the three elements to be connected to the three-pole cable 32.

For this purpose electrical junction elements 37,38 are provided, to ensure electric contact between the wires of the three-pole cable 32 and the electrodes 12, 13 and 36; pin terminals 39 complete the electric contact with the opposite end of each of the wires of the three-pole cable 32, thereby also forming the terminals 39 of an electric connector 33.

In operation (see FIG. 7) part of the sensor 31 is mounted in a fuel rail 2 using the clip 8 as a fastener, like in the main embodiment.

The external electrode 34, which may act as a shielding electrode and/or as a measuring electrode, is in electric contact with one of the wires of the three-pole cable 32 through one of the electrical junction elements 37 and the contact element 36.

The latter comprises a substantially C-shaped band portion, which can at least partially encircle the external electrode 34, preferably by elastic interference, to ensure a good electric contact.

The electrodes 12 and 13 are accommodated in the external tubular electrode 34, and are preferably retained by the support elements 17 and 35 arranged in spaced locations.

The support elements are shown to have each a pair of holes for the passage of the electrodes 12,13: in this variant, the latter have the same length.

The electrical junction elements 37,38 allow the electrodes 12 and 34 to be electrically connected to one of the two ends of the wires of the three-pole cable 32; particularly the electrodes are fitted into and electrically contacted by the metal elastic elements 37 held in rigid metal elements 38, to which the wires of the cable 32 are soldered.

The other ends of the wires of the three-pole cable 32 are connected to pin terminals 39, which may be secured in the connector unit 33.

In this embodiment, each of the terminals 39 is electrically connected to one of the three electrodes 12, 13 and 34.

This possibly allows mutual connection/disconnection of these electric contacts, using a switch (not shown and known per se), to change the transfer function of the sensor, for the above mentioned reasons. Therefore, the electrodes may be connected in various configurations: "in series", "in parallel", with one measuring electrode or with two measuring electrodes, etc., e.g. through preset connections in the circuit or using the above mentioned switches.

For this purpose a circuit (not shown) may be used, which can change electrode connections and/or connect/disconnect two electrodes, preferably one of the internal electrodes 12 and the external electrode 34, to later connect the combination of electrodes to the input port of the appropriate measuring circuit (not shown, and similar to those of FIG. 7).

A second variant, as shown in FIGS. 9 and 10, comprises a sensor 41 in which the measurement electronics has been omitted, which only has two output wires, connected to the electrodes 12, 13 and 14 respectively, like in the first embodiment; alternatively three wires might be provided, one for each electrode, or the circuit 9. A part of the sensor 41 is mounted to one side of a fuel rail 2 having female threads 91, through a sensor body 44 having male threads 92 mating with the female threads.

A third variant, as shown in FIGS. 11 and 12, comprises a sensor 51 (identical to that of the above described embodiment), having female threads (not shown). The sensor 51 is mounted to the side of a fuel rail 2 having male threads 94 mating with the female threads (not shown).

As shown by an overview of the figures, the above described exemplary embodiments of the invention relate to a sensor mounted in a fuel rail, in a position other than the fuel inlet 3. This shall be intended without limitation, because the sensor of the invention may be generally mounted to any flexible or rigid tube or conduit.

The various parts or features described with reference to the above examples may be possibly at least partially combined together, to obtain devices that may be different from those exemplified above.

The invention claimed is:

1. A sensor for detecting properties of a fluid, the sensor comprising:
    a first electrode and a second electrode mainly extending along a first direction, the first electrode and the second electrode being spaced apart so as to not be concentrically disposed, and
    a third electrode at least partially arranged around said first and second electrodes, wherein the first and second electrodes have a form of electrically conductive bars and are arranged side by side along an axis of the third electrode,
    wherein each of the first, second, and third electrodes are in contact with the fluid when the sensor is in operation.

2. The sensor according to claim 1, wherein the first and second electrodes have different lengths.

3. The sensor according to claim 1, wherein the third electrode has a tubular shape that opens in connection with at least one end and/or comprises apertures or holes for the passage of the fluid.

4. The sensor according to claim 1, wherein the cross-section of the third electrode has a shape selected from a group including: circular, polygonal, and lobed.

5. The sensor according to claim 1, wherein the third electrode has a longitudinal aperture extending in one or more of the following ways: axially, circumferentially, helically.

6. The sensor according to claim 1, wherein a capacity of the electrodes is between 10 and 246 pF and/or a resistance of the electrodes is between 1 and 503 kOhm.

7. The sensor according to claim 1, wherein the first and second electrodes are connected in series to each other, whereas the third electrode is connected to a ground.

8. The sensor according to claim 1, wherein either the first or the second electrode can be connected to ground like the third electrode.

9. The sensor according to claim 1, wherein the first and second electrodes are connected to respective detection lines in order to obtain a double measurement.

10. The sensor according to claim 1, comprising means for securing the electrodes to a fuel rail.

11. The sensor according to claim 10, wherein the securing means comprises at least one removable fastener adapted to engage into slots provided in a fuel rail and in a housing adapted to support the electrodes.

12. The sensor according to claim 1, working with low frequency signals applied to the electrodes below 100 Hz.

13. The sensor according to claim 12, working with signals comprised between 5 and 30 Hz.

14. A fuel rail for feeding fuel into an internal combustion engine, the fuel rail comprising:
at least one fuel inlet;
one or more fuel outlets; and
a fuel detection sensor that includes:
a first and a second electrode mainly extending along a first direction, the first electrode and the second electrode being spaced apart so as to not be concentrically disposed, and
a third electrode at least partially arranged around said first and second electrodes and at least partially bounding an elongated passage having a length, wherein the first and second electrodes have the form of elongated electrically conductive bars that extend longitudinally side by side along at least a portion of the length of the passage of the third electrode, the first and second electrodes being positioned so that when the fluid is disposed within the passage, the fluid directly contacts the first electrode, the second electrode and the third electrode; and
fastening means for coupling or securing the fuel detection sensor.

15. The fuel rail according to claim 14, wherein the fastening means is provided in the rail and/or in the sensor and comprises a slot adapted to be removably engaged by a clip.

16. A method for detecting properties of a fluid, using at least one pair of electrodes immersed in the fluid, the method comprising:
electrically energizing the at least one pair of electrodes with an electric current or voltage;
detecting an electric parameter derived from the energization of the at least one pair of electrodes, and
determining a characteristic of the fluid depending on said electric parameter, wherein the detection is made on the fluid flowing along at least one portion of a path in which the at least one pair of elongated electrodes extend longitudinally side by side in direct contact with the fluid, the at least one pair of electrodes comprising a first electrode and a second electrode that are spaced apart so as to not be concentrically disposed.

17. The method according to claim 16, wherein the fluid flow is oriented from one end to the other end of the at least one pair of electrodes.

18. The method according to claim 16, wherein the detection is made on flows running along respective opposite paths or along paths which may vary along the at least one pair of electrodes.

19. The method according to claim 16, wherein the phase of electrically energizing the at least one pair of electrodes is carried out with low frequency signals applied to the electrodes below 100 Hz.

20. The method according to claim 19, wherein the signals are comprised between 5 and 30 Hz.

21. The sensor of claim 1, wherein the first electrode, the second electrode and the third electrode are configured to detect at least one of an electric conductivity of the fluid, a dielectric rigidity of the fluid, or a presence or concentration of substances in the fluid.

22. The method of claim 16, further comprising determining at least one of an electric conductivity of the fluid, a dielectric rigidity of the fluid, or a presence or concentration of substances in the fluid.

23. The fuel rail of claim 14, wherein the fuel detection sensor is disposed inside the at least one inlet such that the first electrode, the second electrode and the third electrode are in a path of the fluid and are in contact with the fluid.

24. The fuel rail of claim 14, wherein the fuel detection sensor is in contact with the liquid in order to perform resistive measurements and capacitive measurements using one or more combinations of at least two of the first electrode, the second electrode and the third electrode.

25. A sensor for detecting properties of a fluid, the sensor comprising:
a first electrode and a second electrode being spaced apart so as to not be concentrically disposed, and
a third electrode at least partially arranged around said first and second electrodes and at least partially bounding an elongated passage having a length, wherein the first and second electrodes have a form of elongated electrically conductive bars that extend longitudinally side by side along a least a portion of the length of the passage of the third electrode,
the first and second electrodes being positioned so that when the fluid is disposed within the passage, the fluid directly contacts the first electrode, the second electrode and the third electrode.

26. The sensor of claim 25, wherein the first electrode, the second electrode and the third electrode are positioned so that when an imaginary plane passes through the third electrode normal to a longitudinal axis thereof, the imaginary plane also passes through the first electrode and the second electrode.

* * * * *